United States Patent [19]
Selegatto et al.

[11] Patent Number: 5,827,963
[45] Date of Patent: Oct. 27, 1998

[54] SYSTEM AND METHOD FOR DETERMINING A DENSITY OF A FLUID

[75] Inventors: Gilberto Selegatto, Serrana; Cesar Sperandio Verissimo, Ribeirão Preto; Joel Concalves de Oliveira Sobrinho, Sertôrio Mazer; Antonio Carlos Cardoso, Ribeirão Preto; Luis Carlos Geron, Setǎozinho; Antonio Dias Cunali Filho, Mococa; Fulvio de Barros Pinheiro Machado, Sertaǎzinho, all of Brazil

[73] Assignee: SMAR Research Corporation, Ronkonkoma, N.Y.

[21] Appl. No.: 656,026

[22] Filed: May 31, 1996

[51] Int. Cl.⁶ .................................................. G01N 9/26
[52] U.S. Cl. ............................................. 73/438; 73/32 R
[58] Field of Search ........................... 73/438, 439, 32 R, 73/434; 340/603; 364/558

[56] References Cited

U.S. PATENT DOCUMENTS

| | | | |
|---|---|---|---|
| 3,896,660 | 7/1975 | Valentyik | 73/438 |
| 3,952,761 | 4/1976 | Friedland | 73/452 |
| 3,958,458 | 5/1976 | Foreman | 73/861.18 |
| 4,365,509 | 12/1982 | Cornelis | 73/438 |
| 4,417,474 | 11/1983 | Elderton | 73/438 |
| 4,420,966 | 12/1983 | Baillie et al. | 73/28 |
| 4,446,730 | 5/1984 | Smith | 73/438 |
| 4,561,307 | 12/1985 | Smith | 73/438 |
| 4,625,553 | 12/1986 | Charter | 73/438 |
| 4,630,478 | 12/1986 | Johnson | 73/438 |
| 4,835,456 | 5/1989 | Liu et al. | 324/61 |
| 5,020,368 | 6/1991 | Evans et al. | 73/438 |
| 5,041,990 | 8/1991 | Yabumoto et al. | 364/510 |
| 5,043,912 | 8/1991 | Reus | 364/509 |
| 5,211,678 | 5/1993 | Stephenson | 73/438 |

OTHER PUBLICATIONS

Douglas M. Considine, "Process/Industrial Instruments and Controls Handbook", 4th ed., pp. 4.157–4.162 (1993). (no month).

"Industrial Pressure Measurement", pp. 54–55 (1982). (no month).

Donald I. Coggan et al., "Fundamentals of Industrial Control", pp. 171–172 (1992). (no month).

*Primary Examiner*—Christine K. Oda
*Attorney, Agent, or Firm*—Kenyon & Kenyon

[57] ABSTRACT

A system and method for obtaining a fluid density of a fluid in a tank includes at least two sensor/transmitter assemblies to obtain fluid pressure measurements at different fluid levels in the tank. After the respective fluid pressures are obtained, the fluid density is calculated as a function of the respective fluid pressure measurements. The sensor/transmitter assemblies have substantially similar variation characteristics so that possible measurement variations are eliminated during fluid density calculations.

30 Claims, 5 Drawing Sheets

SYSTEM AND METHOD FOR DETERMINING A DENSITY OF A FLUID

FIELD OF THE INVENTION

The present invention relates to a system and method for determining a density of a fluid, and in particular, measuring density of a fluid in a tank.

BACKGROUND OF THE INVENTION

Obtaining a measurement of density of a fluid has numerous advantages for various applications. One such application includes, for example, fermentation of beer. Obtaining the density measurements of beer is beneficial in that an indicator used for determining whether the beer should be removed from the beer tank, the "Degree Plateau" value, is directly proportional to the density of beer. Obtaining a precise Degree Plateau value is essential for producing the most favorable results.

Typically, in order to measure the density of beer in the beer tank, a sample of beer is taken from the beer tank and delivered to a testing facility where the density of the beer sample is measured. Even though such density measurements may be precise at the time measurements are performed, by the time the information is available, the Degree Plateau value indicative of the time when the beer should be taken out from the beer tank may not be the most current value. Accordingly, the best brewing results may not be achieved using this density measurement method.

Other methods and systems for measuring density in a fluid have also been implemented. One such method relates to the use of a density sensor and a transmitter which includes two tubes at different fluid levels. The pressure of the fluid is measured at each fluid level by a pressure sensor/transmitter so that a pressure signal may be transmitted to a calculating unit. With this method, it may be possible to differentiate between the pressures at different fluid levels to obtain a density of the fluid. However, such a method may provide erroneous readings depending on the environmental conditions which may affect the pressure sensor/transmitter and affect the measurements. Therefore, virtually error-free density measurements are important in some applications, such as in beer brewing processes, where, for example, obtaining a precise Degree Plateau value is essential to produce the best possible quality of beer. In addition, real time calculation of fluid density is also advantageous.

SUMMARY OF THE INVENTION

According to the present invention, a method and system is provided for obtaining a fluid density in a tank. A first sensor assembly is provided at a first measuring level of the tank, where the first sensor assembly measures a fluid pressure. The first sensor assembly also includes a first transmitter generating a first fluid pressure signal having a first value. A second sensor assembly is also provided at a second measuring level of the tank at a predetermined distance from the first sensor assembly. The second sensor assembly measures the fluid pressure at the second measuring level. The second sensor assembly also includes a second transmitter generating a second fluid pressure signal having a second value. The fluid density is calculated as a function of the first value and the second values of the fluid pressure signals.

In an exemplary embodiment of the present invention, each sensor assembly has a substantially similar variation characteristic compared to the other sensor assembly. Thus, all sensor assemblies are "matched", thereby virtually eliminating erroneous fluid density calculations. This is due to the fact that during the fluid density calculation, the variable components of the fluid pressure measurements resulting from each sensor are the same and thus their effect is eliminated by the calculation. Accordingly, virtually error-free fluid density calculations in a fluid tank are obtained.

In another exemplary embodiment of the present invention, each sensor assembly includes a sensor connected to the respective transmitter with a short tube. The external temperature has less of a negative effect on the short tube, thus limiting the pressure measurement errors. In addition, a sanitary seal is utilized to connect each one of the sensor assemblies to the tank, which allows for additional advantages, such as, e.g., decreasing possibility of contamination if a tank is opened.

DETAILED DESCRIPTION

Figure 1:
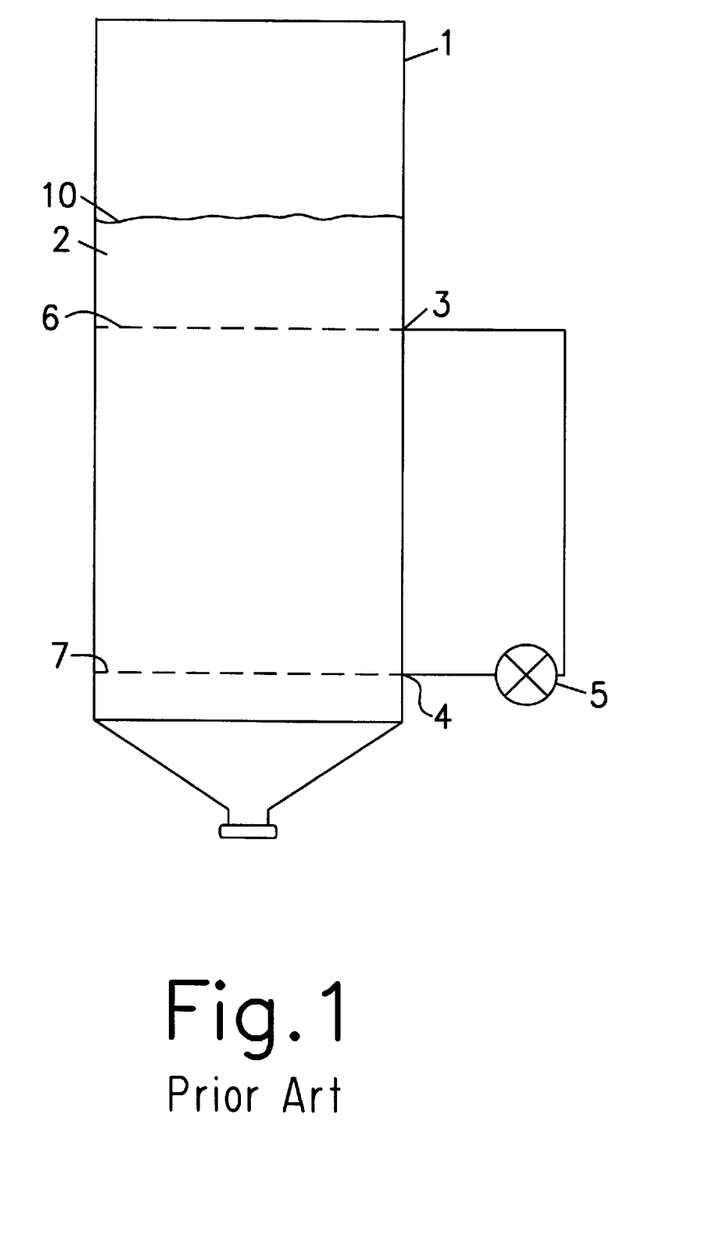
FIG. 1 illustrates a prior art method for measuring density of a fluid in a tank.

FIG. 1 illustrates a prior art method for measuring density of fluid in a tank. As shown, tank 1 encloses a fluid 2 at a particular fluid level 10. A sensor/transmitter assembly 5 is connected to a first level position 3 on the tank for measuring fluid pressure at a first fluid level 6. The sensor/transmitter assembly 5 is also coupled to a second level position 4 on the tank 1 for measuring fluid pressure at a second fluid level 7. The difference between the fluid pressure at first fluid level 6 and the fluid pressure at second fluid level 7 is used for a determination of the fluid density of the fluid 2 in tank 1.

One possible application of this method is, e.g., measuring density of beer in a beer tank to obtain a Degree Plateau value. Density changes of fluid in the beer tank are actuated by controlling the temperature within the tank. However, changes in temperature, as well as other environmental changes, may negatively effect sensor/transmitter assembly 5 since the accuracy of the pressure measurements taken by sensor/transmitter assembly 5 may become less accurate due to the environmental changes. In some applications, and especially for beer fermentation, virtually error-free density measurements are essential for obtaining desired results. A small variation in density (e.g., 5–6%) could generate a large change in, e.g., the Degree Plateau value. It would not be possible to determine whether a density variation occurred due to an erroneous temperature variation in sensor/transmitter 5 or whether the variation was a true fluid density change. Thus, in the case of beer fermentation, even a slight error in beer density calculations (and beer pressure measurements) may generate erroneous Degree Plateau values which would prevent a production of the best possible beer.

Figure 2:
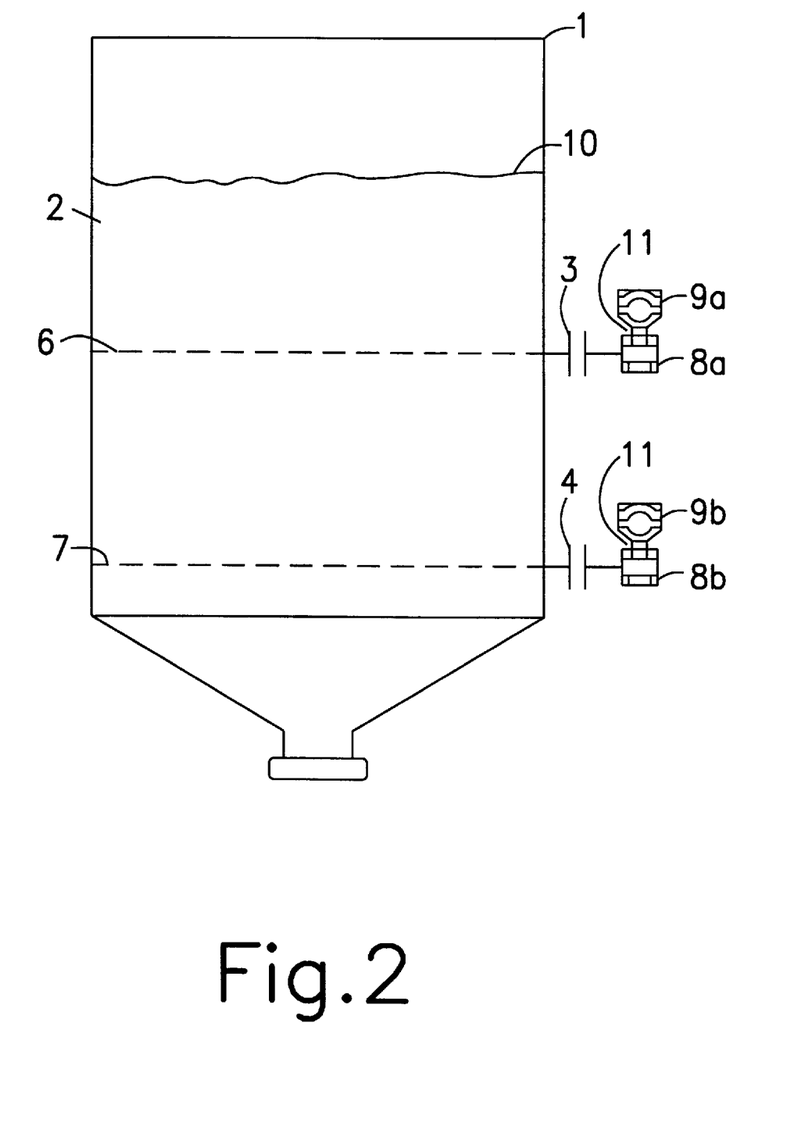
FIG. 2 illustrates a system for measuring fluid density according to an exemplary embodiment of the present invention.

FIG. 2 illustrates a system for accurately measuring fluid density in a tank according to the present invention. Tank 1 encloses fluid 2 having a top fluid level 10. The system includes a first sensor 8a which is connected to a first level position 3 on the tank for measuring fluid pressure at a first fluid level 6. A first transmitter 9a is connected to the first sensor 8a for transmitting pressure measurement obtained at the first fluid level 6. The system also includes a second sensor 8b which is coupled to a second level position 4 on the tank 1 for measuring fluid pressure at a second fluid level 7. A respective second transmitter 9a is connected to the second sensor 8a for transmitting pressure measurement obtained at the second fluid level 7.

First fluid level 6 and second fluid level 7 are below the top fluid level 10 so that fluid pressure measurement can be made with the first sensor 8a and second sensor 8b. Each sensor 8a, 8b converts the measured pressure into respective electrical signals. The difference between the measured fluid pressure (conveyed via respective electrical signals by the first and second transmitters 9a, 9b) at first fluid level 6 and at second fluid level 7 is used for a determination of the fluid density of fluid 2 in the tank 1. According to the present invention, the sensor/transmitter pairs 8a, 9a and 8b, 9b may each be, for example, a single unit or separate components coupled to one another.

According to the present invention, first sensor/transmitter pair 8a, 9a and second sensor/transmitter pair 8b, 9b (such as, for example, SMAR LD301S or SMAR LD302S Sanitary Differential Pressure Transmitters manufactured by SMAR Research Corporation) each have the same variation characteristics, i.e., the same temperature variations. Therefore, first sensor/transmitter pair 8a, 9a is "matched" to second sensor/transmitter pair 8b, 9b. When the measured pressure value obtained with first sensor 8a (and transmitted by first transmitter 9a) is subtracted from second pressure value obtained from second sensor 8b (and transmitted by second transmitter 9b), the variations (or variation errors) of both sensor/transmitter pairs 8a, 9a and 8b, 9b are eliminated by the subtraction. Accordingly, the fluid density value that is calculated based on pressure readings taken by first sensor 8a and second sensor 8b would be virtually free from the environmental and manufacturing effects that may cause erroneous fluid density calculations, thus generating precise and error-free Degree Plateau values. The method and a system according to the present invention would, for example, produce virtually ideal Degree Plateau values so that the best results for fermenting beer can be obtained, which result could not otherwise be obtained using conventional systems and methods for determining fluid density.

Figure 5:
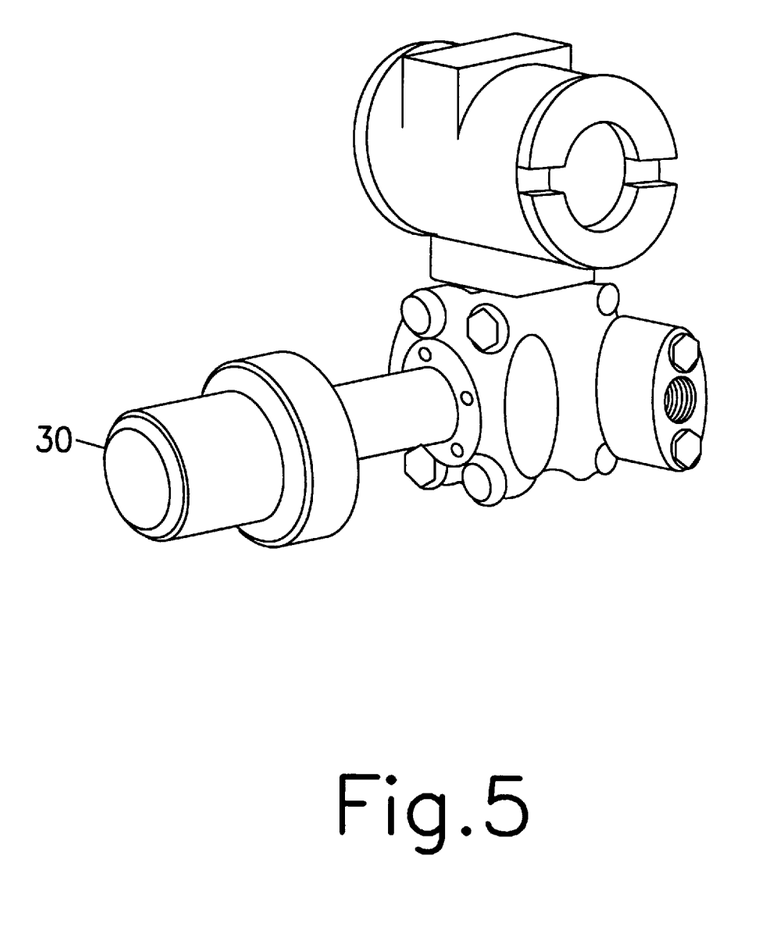
FIG. 5 illustrates a sensor assembly having a sanitary seal according to yet another embodiment of the present invention.

According to another embodiment of the present invention, first sensor 8a and second sensor 8b are coupled to their respective transmitters 9a, 9b using a short tube 11, which is shown in FIG. 2. It is advantageous to utilize short tube 11 (versus a long tube) so that, e.g., the temperature and other environmental variables would have a minimal effect on the electrical pressure signals delivered from first and second sensors 8a, 8b to their respective transmitters 9a, 9b. It would also be advantageous to insert a capillary tube inside the short tube 11 having rigid properties in order to further minimize the effects of ambient temperature on the electrical pressure signals. Using short tube 11, a sanitary seal 30 (illustrated in FIG. 5) may be employed to seal the first and second sensors 8a, 8b to fluid tank 1. The sanitary seals are easily cleaned and are advantageously used to prevent bacteria build up in the transmitters. The sanitary seals are used in, for example, SMAR LD301S or SMAR LD302S Sanitary Differential Pressure Transmitters. It is advantageous to utilize a sanitary seal 30 according to the present invention, since the sanitary seal 30 being positioned in close proximity to first and second transmitters 9a, 9b allows relatively easy manipulation and quick connection of the sanitary seal 30.

Figure 3:
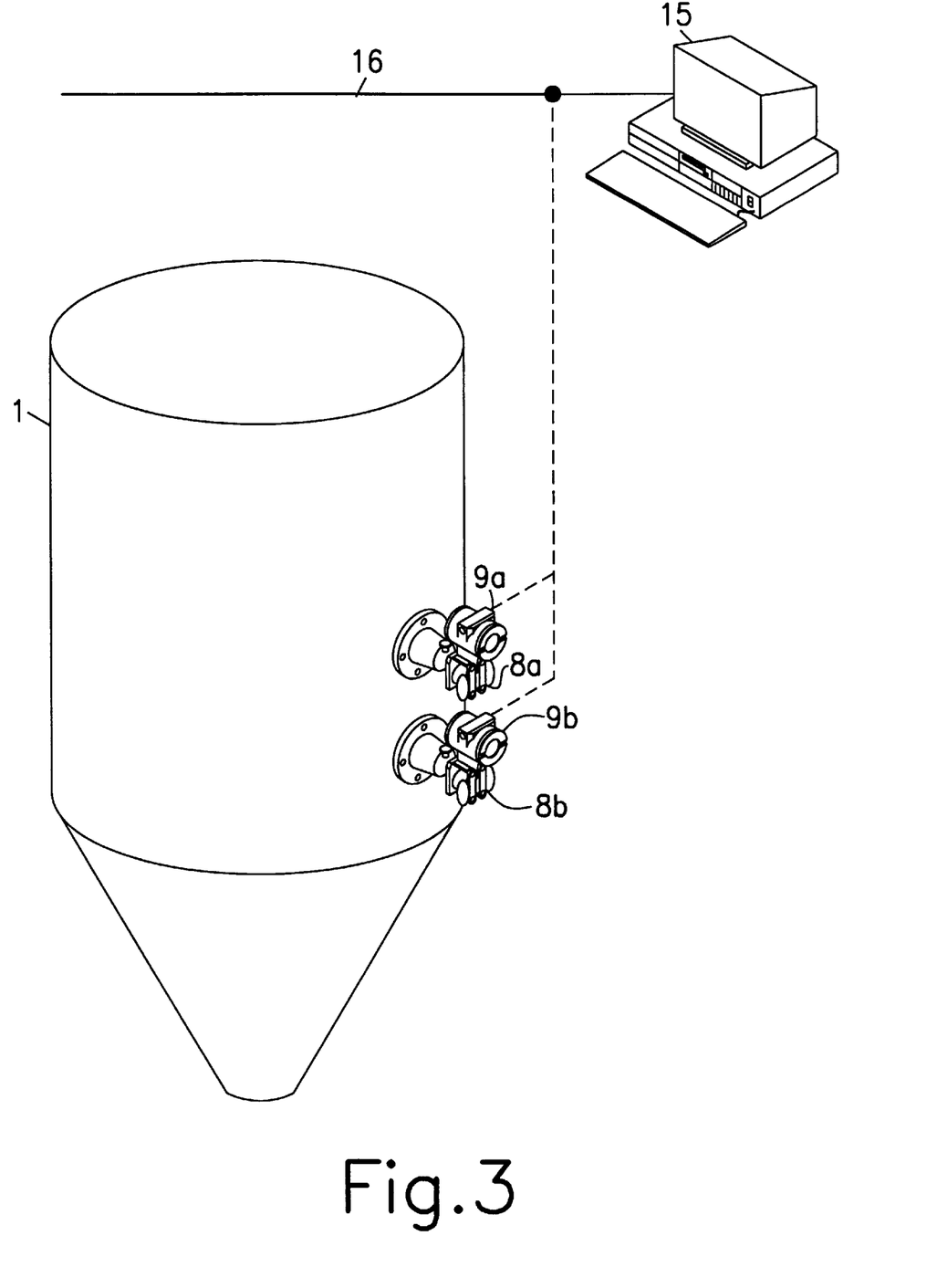
FIG. 3 illustrates a system for measuring fluid density according to another exemplary embodiment of the present invention.

As indicated in FIG. 3, the first and second transmitters 9a, 9b are usually positioned on top of the first and second sensors 8a, 8b, respectively, for communicating with a monitoring/processing device 15, e.g., a computer. First and second transmitters 9a, 9b may each be coupled to the computer directly or connected to a data bus 16, which in turn is coupled to the computer. Furthermore, first and second transmitters 9a, 9b may each be associated with monitoring/processing device 15 via wireless communications.

Figure 4:
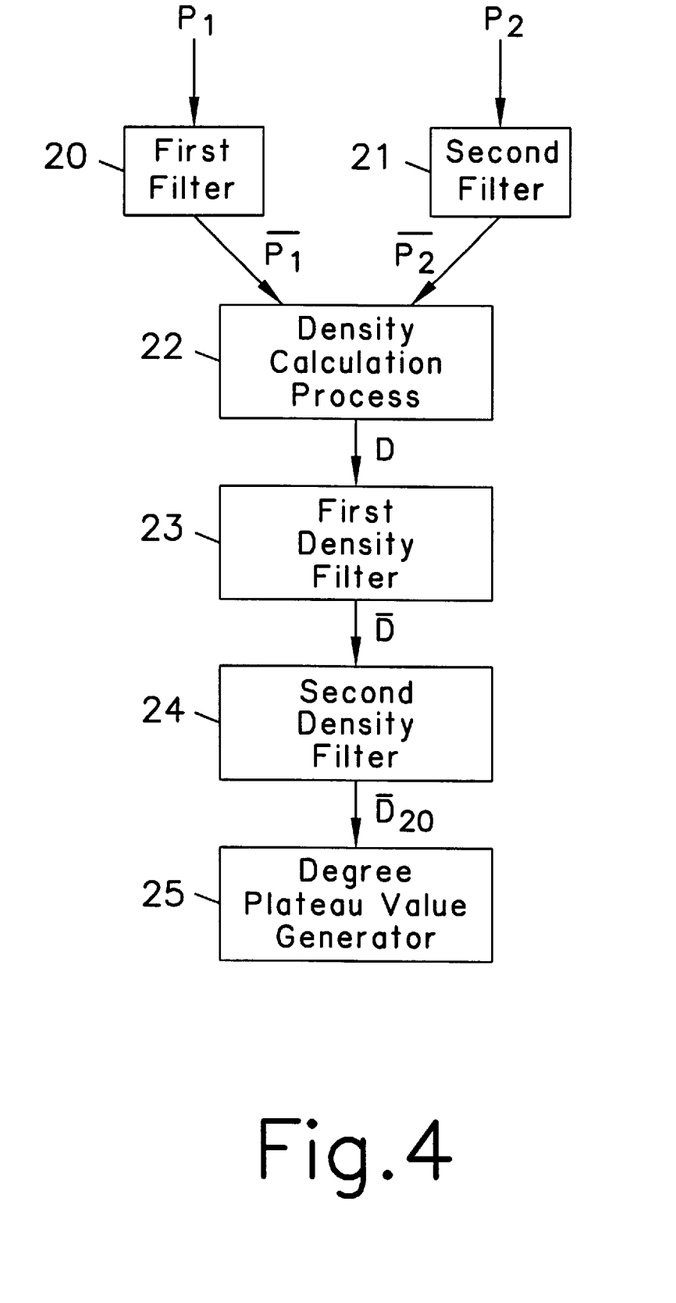
FIG. 4 illustrates a process flow chart according to the present invention.

A method for generating density values of the fluid in the tank corresponding to Degree Plateau values according to the present invention is illustrated in FIG. 4. As shown, first electric pressure signal $P_1$ (measured and transmitted by first sensor assembly 8a, 9a) and second electric pressure signal $P_2$ (measured and transmitted by second sensor assembly 8b, 9b) each pass through a respective first and second filters 20, 21 to generate a first and second electric mean pressure values $\overline{P}_1$, $\overline{P}_2$. First and second filters 20, 21 filter fluid pressure signals to obtain mean pressure values according to the following formula:

$$\overline{P} = \frac{\sum_{i=1}^{N_p} P_i}{N_p},$$

where $N_p \geq 1$ (number of pressure measurements over time).

Next, the density D is calculated in a density calculation process 22 based on first and second electric mean pressure values $\overline{P}_1$, $\overline{P}_2$ according to, for example, the following formula:

$$D = \frac{(\overline{P}_1 - \overline{P}_2)*K}{h},$$

where:

K is a constant, and h is a distance between first fluid level 6 and second fluid level 7.

Density D is then filtered in a first density filter 23 to obtain a mean density $\overline{D}$ according to the following formula:

$$\overline{D} = \frac{\sum_{i=1}^{N_d} D_i}{N_d},$$

where $N_d \geq 1$.

The mean density is further filtered in a second density filter 24 to obtain Mean Density Function Value ($\overline{D}_{20}$), according to, for example, the following formula:

$$\overline{D}_{20} = \frac{\overline{D}*[1 + 0.207*10^{-3} * (T - 20)]}{0.00928},$$

where:

$\overline{D}_{20}$ is a relative density reflected at 20° C., and

T is a temperature of the fluid.

Finally, the Degree Plateau value is calculated as a function of the Mean Density Function Value ($\overline{D}_{20}$) in Degree Plateau Value Generator 25. Using this process, virtually error-free density calculations of fluid in a tank can be obtained to generate precise Degree Plateau values for fermenting beer. Even if there are environmental changes that may effect the sensors, the erroneous variations of pressure measurements of each sensor will be negated since the sensors are "matched".

What is claimed is:

1. A method for determining a density of a substantially static fluid in a tank having a first measuring level and a second measuring level, the tank containing a fluid level above the first measuring level and the second measuring level, the method comprising the steps of:

measuring a first fluid pressure of the substantially static fluid at the first measuring level via a first sensor assembly, the first sensor assembly being mounted, external to the tank, via a first single connection at the first measuring level and including a first transmitter generating a first fluid pressure signal corresponding to the first fluid pressure, the first fluid pressure signal having a first value;

measuring a second fluid pressure of the substantially static fluid at the second measuring level via a second sensor assembly, the second sensor assembly being mounted, external to the tank, via a second single connection at the second measuring level and including a second transmitter generating a second fluid pressure signal corresponding to the second fluid pressure, the second fluid pressure signal having a second value; and calculating the fluid density in the tank as a function of the first value of the first fluid pressure signal and the second value of the second fluid pressure signal.

2. The method according to claim 1, further comprising the step of:

associating each one of the first transmitter and the second transmitter with a computing device.

3. The method according to claim 2, wherein the computing device monitors the fluid density in the tank.

4. The method according to claim 1, wherein the first sensor assembly is positioned at a predetermined distance from the second sensor assembly.

5. The method according to claim 1, wherein the tank contains beer and wherein the fluid density represents a beer density.

6. The method according to claim 1, wherein the first sensor assembly includes a first sensor connected to the first transmitter via a first connector tube, and wherein the second sensor assembly includes a second sensor connected to the second transmitter via a second connector tube.

7. The method according to claim 6, wherein each one of the first connector tube and the second connector tube has a minimal length.

8. The method according to claim 7, wherein the first sensor assembly is connected to the tank via a first sanitary seal, and wherein the second sensor assembly is connected to the tank via a second sanitary seal.

9. The method according to claim 1, wherein the fluid density is proportional to a degree plateau value of the substantially static fluid, the degree plateau value indicating a fermentation level of the substantially static fluid.

10. A method for determining a density of a substantially static fluid in a tank having a first measuring level and a second measuring level, the tank containing a fluid level above the first measuring level and the second measuring level, the method comprising the steps of:

measuring a first fluid pressure of the substantially static fluid at the first measuring level via a first sensor assembly, the first sensor assembly being positioned via a first single connection at the first measuring level and including a first transmitter generating a first fluid pressure signal corresponding to the first fluid pressure, the first fluid pressure signal having a first value;

measuring a second fluid pressure of the substantially static fluid at the second measuring level via a second sensor assembly, the second sensor assembly being positioned via a second single connection at the second measuring level and including a second transmitter generating a second fluid pressure signal corresponding to the second fluid pressure, the second fluid pressure signal having a second value; and calculating the fluid density in the tank as a function of the first value of the first fluid pressure signal and the second value of the second fluid pressure signal, wherein the first sensor assembly has a first variation characteristic and the second sensor assembly has a second variation characteristic, the first variation characteristic being matched to the second variation characteristic to reduce erroneous measurements of the first and second fluid pressures by the first and second sensor assemblies.

11. The method according to claim 10, wherein the fluid density is proportional to a degree plateau value of the substantially static fluid, the degree plateau value indicating a fermentation level of the substantially static fluid.

12. The method according to claim 10, wherein the first and second fluid pressure signals have a same error variation, and wherein the error variation is eliminated when the fluid density is calculated.

13. A method for determining a fluid density of beer in a tank and having a first measuring level and a second measuring level, the tank containing a fluid level above the first measuring level and the second measuring level, the method comprising the steps of:

measuring a fluid pressure at the first measuring level via a first sensor assembly, the first sensor assembly being positioned at the first measuring level and including a first transmitter generating a first fluid pressure signal having a first value;

measuring the fluid pressure at the second measuring level via a second sensor assembly, the second sensor assembly being positioned at the second measuring level and including a second transmitter generating a second fluid pressure signal having a second value; and calculating the fluid density of the beer in the tank as a function of the first value of the first fluid pressure signal and the second value of the second fluid pressure signal, wherein the fluid density of the beer is proportional to a degree plateau value of the beer, the degree plateau value indicating a fermentation level of the beer.

14. A system for determining a density of a substantially static fluid in a tank having a first measuring level and a second measuring level, the tank containing fluid level above the first measuring level and the second measuring level, the system comprising:

a first sensor assembly mounted, external to the tank, at the first measuring level of the tank, the first sensor assembly measuring a first fluid pressure of the substantially static fluid via a first single connection at the first measuring level and including a first transmitter generating a first fluid pressure signal corresponding to the first fluid pressure, the first fluid pressure signal having a first value;

a second sensor assembly mounted, external to the tank, at the second measuring level of the tank, the second sensor assembly measuring a second fluid pressure of the substantially static fluid via a second single connection at the second measuring level and including a second transmitter generating a second fluid pressure signal corresponding to the second fluid pressure, the second fluid pressure signal having a second value; and a calculating device coupled to the first and second sensor assemblies, the calculating device calculating the fluid density in the tank as a function of the first value of the first fluid pressure signal and the second value of the second fluid pressure signal, wherein the first value is provided to the calculating device by the first transmitter and the second value is provided to the calculating device by the second transmitter.

15. The system according to claim 14, wherein the calculating device includes a general purpose computer.

16. The system according to claim 14, wherein the first sensor assembly is positioned at a predetermined distance from the second sensor assembly.

17. The system according to claim 14, wherein the first sensor assembly includes a first sensor connected to the first transmitter via a first connector tube, and wherein the second sensor assembly includes a second sensor connected to the second transmitter via a second connector tube, each one of the first and second connector tubes having a minimal length.

18. The system according to claim 17, wherein the first sensor assembly is connected to the tank via a first sanitary seal, and wherein the second sensor assembly is connected to the tank via a second sanitary seal.

19. The system according to claim 14, wherein the fluid density is proportional to a degree plateau value of the substantially static fluid, the degree plateau value indicating a fermentation level of the substantially static fluid.

20. A system for determining a density of a substantially static fluid in a tank having a first measuring level and a second measuring level, the tank containing fluid level above the first measuring level and the second measuring level, the system comprising:

a first sensor assembly positioned at the first measuring level of the tank, the first sensor assembly measuring a first fluid pressure of the substantially static fluid at the first measuring level and including a first transmitter generating a first fluid pressure signal corresponding to the first fluid pressure, the first fluid pressure signal having a first value;

a second sensor assembly positioned at the second measuring level of the tank, the second sensor assembly measuring a second fluid pressure of the substantially static fluid at the second measuring level and including a second transmitter generating a second fluid pressure signal corresponding to the second fluid pressure, the second fluid pressure signal having a second value; and a calculating device coupled to the first and second sensor assemblies, the calculating device calculating the fluid density in the tank as a function of the first value of the first fluid pressure signal and the second value of the second fluid pressure signal, wherein the first value is provided to the calculating device by the first transmitter and the second value is provided to the calculating device by the second transmitter, wherein the first sensor assembly has a first variation characteristic and the second sensor assembly has a second variation characteristic, the first variation characteristic being matched to the second variation characteristic to reduce erroneous measurements of the first and second fluid pressures by the first and second sensor assemblies.

21. The system according to claim 20, wherein the fluid density is proportional to a degree plateau value of the substantially static fluid, the degree plateau value indicating a fermentation level of the substantially static fluid.

22. The system according to claim 20, wherein the first sensor assembly is mounted to the tank via a first single connection at the first measuring level, and wherein the second sensor assembly is mounted to the tank via a second single connection at the second measuring level.

23. The method according to claim 20, wherein the first and second fluid pressure signals have a same error variation, and wherein the error variation is eliminated when the fluid density is calculated.

24. A system for determining a degree plateau value for brew in a brew tank, the degree plateau value being proportional to a brew density of brew in the brew tank, the brew being a substantially static fluid, the system comprising:

a first sensor assembly positioned at a first measuring level of the brew tank, the first sensor assembly measuring a first brew pressure of the substantially static fluid at the first measuring level and including a first transmitter generating a first brew pressure signal corresponding to the first brew pressure, the first brew pressure signal having a first value, the first sensor assembly having a first variation characteristic;

a second sensor assembly positioned at a second measuring level of the brew tank, the second sensor assembly measuring a second brew pressure of the substantially static fluid at the second measuring level and including a second transmitter generating a second brew pressure signal corresponding to the second brew pressure, the second brew pressure signal having a second value, the second sensor assembly having a second variation characteristic being matched to the first variation characteristic of the first sensor assembly to reduce erroneous measurements of the first and second brew pressures by the first and second sensor assemblies; and a calculating device coupled to the first and second sensor assemblies, the calculating device calculating the brew density in the brew tank as a function of the first value of the first brew pressure signal and the second value of the second brew pressure signal, wherein the first value is provided to the calculating device by the first transmitter and the second value is provided to the calculating device by the second transmitter.

25. The system according to claim 24, wherein the first sensor assembly includes a first sensor connected to the first transmitter via a first connector tube, and wherein the second sensor assembly includes a second sensor connected to the second transmitter via a second connector tube, each one of the first and second connector tubes having a minimal length.

26. The system according to claim 25, wherein the first sensor assembly is connected to the brew tank via a first sanitary seal, and wherein the second sensor assembly is connected to the brew tank via a second sanitary seal.

27. The system according to claim 24, wherein the degree plateau value indicates a fermentation level of the brew.

28. The system according to claim 24, wherein the first sensor assembly is mounted to the brew tank via a first single connection at the first measuring level, and wherein the second sensor assembly is mounted to the brew tank via a second single connection at the second measuring level.

29. A method for determining a density of a substantially static fluid in a tank having a first measuring level and a second measuring level, the tank containing a fluid level above the first measuring level and the second measuring level, the method comprising the steps of:

measuring a first fluid pressure of the substantially static fluid at the first measuring level via a first sensor assembly, the first sensor assembly being positioned at the first measuring level and including a first transmitter generating a first fluid pressure signal corresponding to the first fluid pressure, the first fluid pressure signal having a first value;

measuring a second fluid pressure of the substantially static fluid at the second measuring level via a second sensor assembly, the second sensor assembly being positioned at the second measuring level and including a second transmitter generating a second fluid pressure signal corresponding to the second fluid pressure, the second fluid pressure signal having a second value;

calculating the fluid density in the tank as a function of the first value of the first fluid pressure signal and the second value of the second fluid pressure signal; and associating each one of the first transmitter and the second transmitter with a computing device, wherein the first value is transmitted to the computing device via a wireless connection, and wherein the second value is transmitted to the computing device via the wireless connection, wherein the fluid density is proportional to a degree plateau value of the substantially static fluid, the degree plateau value indicating a fermentation level of the substantially static fluid.

30. A method for determining a density of a substantially static fluid in a tank having a first measuring level and a second measuring level, the tank containing a fluid level above the first measuring level and the second measuring level, the method comprising the steps of:

measuring a first fluid pressure of the substantially static fluid at the first measuring level via a first sensor assembly, the first sensor assembly being positioned at the first measuring level and including a first transmitter generating a first fluid pressure signal corresponding to the first fluid pressure, the first fluid pressure signal having a first value;

measuring a second fluid pressure of the substantially static fluid at the second measuring level via a second sensor assembly, the second sensor assembly being positioned at the second measuring level and including a second transmitter generating a second fluid pressure signal corresponding to the second fluid pressure, the second fluid pressure signal having a second value;

calculating the fluid density in the tank as a function of the first value of the first fluid pressure signal and the second value of the second fluid pressure signal; and associating each one of the first transmitter and the second transmitter with a computing device, wherein the first value is transmitted to the computing device via a wireless connection, and wherein the second value is transmitted to the computing device via the wireless connection, wherein the first sensor assembly is mounted to the tank via a first single connection at the first measuring level, and wherein the second sensor assembly is mounted to the tank via a second single connection at the second measuring level.

\* \* \* \* \*